United States Patent [19]

Hsu et al.

[11] Patent Number: 5,632,766
[45] Date of Patent: May 27, 1997

[54] VENTRICULAR DEFIBRILLATION BY COORDINATION OF SHOCKS WITH SENSED COARSE VF COMPLEXES

[75] Inventors: William Hsu, Circle Pines; Yayun Lin, St. Paul, both of Minn.

[73] Assignee: Cardiac Pacemakers, Inc., St. Paul, Minn.

[21] Appl. No.: 513,685

[22] Filed: Aug. 11, 1995

[51] Int. Cl.$^6$ .................................................. A61N 1/39
[52] U.S. Cl. ................................................................ 607/5
[58] Field of Search ........................................ 607/4, 5

[56] References Cited

U.S. PATENT DOCUMENTS

| | | | |
|---|---|---|---|
| 4,202,340 | 5/1980 | Langer et al. | 607/5 |
| 4,940,054 | 7/1990 | Grevis et al. | 607/4 |
| 4,949,719 | 8/1990 | Pless et al. | 607/7 |
| 5,179,945 | 1/1993 | Hofwegen et al. | 607/5 |
| 5,188,105 | 2/1993 | Keimel | 607/5 |
| 5,193,535 | 3/1993 | Bardy et al. | 607/4 |
| 5,346,506 | 9/1994 | Mower et al. | 607/7 |
| 5,439,483 | 8/1995 | Duong-Van | 607/5 |
| 5,489,293 | 2/1996 | Pless et al. | 607/5 |
| 5,500,008 | 3/1996 | Fain | 607/5 |

FOREIGN PATENT DOCUMENTS

| | | | |
|---|---|---|---|
| 0347708 | 12/1989 | European Pat. Off. | A61B 5/02 |
| 0550343 | 7/1993 | European Pat. Off. | A61N 1/38 |
| 0550344 | 7/1993 | European Pat. Off. | A61N 1/39 |
| WO93/20888 | 10/1993 | WIPO | A61N 1/365 |

OTHER PUBLICATIONS

Hsia, Peng–Wie et al., "Genesis of Sigmoidal Dose–Response Curve During Defibrillation by Random Shock: A Theoretical Model Based on Experimental Evidence for a Vulnerable Window During Ventricular Fibrillation," *Pace*, vol. 13, pp. 1326–1342, (Oct. 1990).

Hsia, Peng–Wie et al., "Improved Nonthoractomy Defibrillation Based on Ventricular Fibrillation Waveform Characteristics," *Pace*, 18, p. 803, Abstract No. 29, (Apr. 1995, Part II).

Hsia, Peng–Wie et al., "Absolute Depolarization Vector Characteristics Associated with Successful Defibrillation: Evidence of a Vulnerable Period During Ventricular Fibrillation," *Supplement III Circulation*, vol. 82, No. 4, p. III–738, (Oct. 1990).

Jones, Douglas L. et al., "Ventricular Fibrillation: The Importance of Being Coarse?," *J. Electrocardiology*, 17, No. 4, pp. 393–400, (1984).

Kuelz, Kathy W. et al., "Integration of Absolute Ventricular Fibrillation Voltage Correlates with Successful Defibrillation," *IEEE Transactions on Biomedical Engineering*, 41, No. 8, pp. 782–791, (Aug. 1994).

Mower, Morton M. et al., "Synchronizaton of Low–Energy Pulses to Rapid Deflectoin Signals as a Possible Mechanism of Subthreshold Ventricular Defibrillation," *Abstracts of the 55th Scientific Sessions*, II–75, Abstract No. 298, (1982).

*Primary Examiner*—William E. Kamm
*Assistant Examiner*—Carl H. Layno
*Attorney, Agent, or Firm*—Schwegman, Lundberg, Woessner & Kluth, P.A.

[57] ABSTRACT

A method and system for ventricular defibrillation by coordinating the delivery of defibrillation shocks with sensed ventricular fibrillation complexes in a way which improves the probability of success of the defibrillation shock. Ventricular electrical activity is monitored during VF to detect coarse VF complexes. The defibrillation shock is delivered in coordination with the occurrence of coarse VF complexes, and specifically to occur on the upslope portion thereof, for optimal probability of success. Preferably, DF shock is delivered on the nth occurring coarse VF complex, wherein n is equal to or greater than 2 and less than or equal to about 9.

22 Claims, 6 Drawing Sheets

VENTRICULAR DEFIBRILLATION BY COORDINATION OF SHOCKS WITH SENSED COARSE VF COMPLEXES

FIELD OF THE INVENTION

This invention pertains to the field of treatment of ventricular fibrillation by the delivery of electric defibrillation shocks. In particular, the invention pertains to a method and system for coordinating the delivery of defibrillation shocks with sensed ventricular fibrillation complexes in a way which improves the probability of success of the defibrillation shock.

BACKGROUND OF THE PRIOR ART

Electric shock defibrillation is a proven technique of treatment of the serious and immediately life-threatening condition of ventricular fibrillation (VF). For patients known to be at risk, an implantable defibrillator may be used. Such devices contain an energy source, an electrode lead system in contact in the heart, a sensing system to detect the onset of fibrillation, and a pulse generator for delivering the defibrillation (DF) shock. Often they are combined with a pacemaker function in the same device.

Existing devices are generally designed or programmed to deliver a shock or series of shocks at a fixed interval or intervals following the detection of the fibrillation, unless fibrillation spontaneously terminates on its own first, or until recovery is achieved, as evidenced by the resumption of normal ventricular rhythm. The amount of energy to be delivered in a shock must be carefully chosen. If too small, it may not be successful in terminating the fibrillation. On the other hand, the shock must not be too large, from physiological considerations, and also in consideration of the limited energy storage in an implanted device.

It is also known in the treatment of tochyarrhythmia to use an implantable atrial defibrillator to deliver pulses of defibrillating energy to the atria synchronized with sensed R waves of the ventricle. However, in the case of VF, there is not an R wave to synchronize to, so the DF shock must be delivered asynchronously.

It is known that ventricular electrical signals during fibrillation may exhibit a pattern, known as "fine VF," characterized by relatively low signal amplitude and lack of organized features; and they may also exhibit a pattern known as "coarse VF," subjectively characterized by intervals of higher amplitude, which may repeat, separated by fine VF intervals. It has also been suspected that it is easier to defibrillate coarse VF than fine VF. Because of this, previous works have suggested the possibility of timing of DF shocks to features of the VF waveforms as a way to improve DF efficacy. However, it has not been clear from such prior works, which features are important, and how to detect and coordinate to them.

One experimenter retrospectively noted diastolic periods in the monophasic action potential (MAP) tracings, and suggested these periods were more conducive to defibrillation. Another retrospectively observed that some subthreshold defibrillations which were successful had a fixed timing relationship with a bipolar sensing signal in the right ventricle of dogs. However, another study examined spatial coherence in VF on surface of heart using epicardial sensing electrodes, and concluded that coarseness and fineness of VF was mainly due to lead orientation, and not to the degree of organization of electrical activity as measured. Therefore, there appears to be no firm correlation per se recognized in the prior art between DF shock timing and VF features, especially one that may be successfully applied prospectively. One recent study retrospectively examined the correlation between the voltages measured on the surface leads and the energy required to defibrillate dogs instrumented with epicardial patches. Some reduction in energy requirements was found with defibrillation shocks that happened at places where measured voltages were "high."

It is clear that while a number of investigators have pointed to the possibility of using VF waveform features as a guide to delivering DF shocks, there are problems to be solved in the practical and effective prospective detection of VF features, and the determination of which features thereof are significant, in terms of coordination of DF shocks, for maximizing efficacy.

SUMMARY OF THE INVENTION

As explained in detail below, we have provided an improved method and system for detecting an optimal timing for the delivery of shocks, such that the shocks delivered have an improved probability of success in terminating the fibrillation. This improved efficacy provides important medical advantages to the patient, both in the greater probability of success of individual shocks, and also in the reduction in pulse energy and number of shocks needed to defibrillate. The method and system of the invention is based in part on the detection of characteristics of coarse VF complexes which may exist during fibrillation, and the coordination of DF shocks with portions of those complexes.

To overcome the problems in the prior art, the present invention provides an improved method and system for detecting coarse VF complexes, and for coordinating the delivery of DF shocks.

According to one feature of the invention, ventricular electrical activity is monitored during a period of ventricular fibrillation, and the occurrence of coarse VF complexes is detected. A favorable instant of time for delivery of a DF shock is selected when the magnitude or absolute value of the monitored VF signal reaches a predetermined value during a period of increasing signal. In this way the DF shock may be coordinated with the upslope portion of a VF complex.

According to another feature of the invention, the nth occurring coarse VF complex is selected for the coordinated DF shock, where n is equal to 2 or more, and less than or equal to about 9. As a practical matter, the coordinated DF shock should be delivered prior to that count, because of the time element.

According to another aspect of the invention, an improved defibrillator system includes a lead system for placement in electrical contact with the ventricle of the heart and a sensing system attached to lead for monitoring ventricular electrical activity. The sensing system detects the occurrence of VF, and during VF, also detects coarse VF complexes. The system includes a controlled DF pulse generator for delivering DF shocks to the lead system to the ventricle. A control system for controlling the pulse generator, operates in responsive to the sensing system and triggers the DF pulse generator to deliver a DF shock when the sensed VF complex increases to a predetermined value with a positive rate of change. In this manner, the DF shock is coordinated with the upslope of a VF complex, which we have found will substantially improve the probability of success of the DF shock.

According to a preferred form of this system, control system is operative to count the occurrence of VF complexes, and to trigger delivery of a DF shock coordinated with the nth coarse VF complex, where n is equal to or greater than 2 and less than or equal to about 9. If success in not achieved with coordinated DF shocks, the system switches to asynchronous shocks.

These and other features and advantages of the invention will become apparent from the following description of the preferred embodiments of the invention.

DESCRIPTION OF THE PREFERRED EMBODIMENT

The preferred embodiment of the invention is illustrated herein as included in an implantable heart defibrillator/pacemaker, which may include numerous pacing modes as is generally known in the art. The system and method of the invention could also be implemented in an external defibrillator/monitor.

Figure 1:
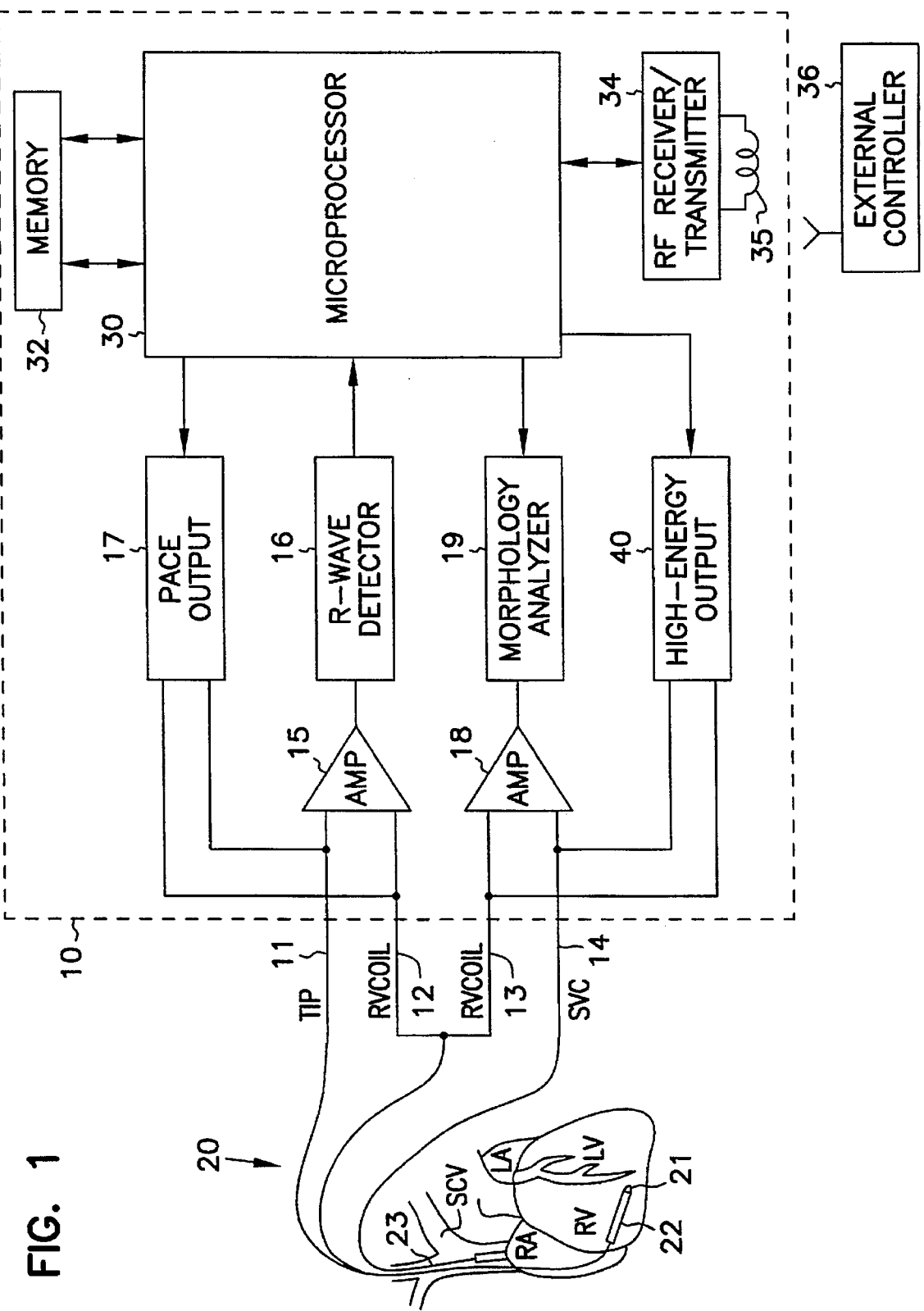
FIG. 1 is a block diagram of an implantable defibrillator/pacemaker of the type with which the present invention may be implemented, including a diagrammatic representation of a lead system placed in a heart.

In FIG. 1, defibrillator/pacemaker 10 is shown in block diagram form. It includes terminals, labeled with reference numbers 11, 12, 13, and 14, for connection to a lead system 20. Lead system 20 is preferably an endocardial lead, although other types could also be used within the scope of the invention. An endocardial lead is adapted for placement in the right ventricle. The lead system includes a number of electrodes or electrical contacts. The tip electrode 21 is at the distal end of the lead system, and connects electrically through a conductor provided in the lead, for connection to terminal 11. Lead system 20 also includes an RV coil electrode 22 space near the distal end for placement in the right ventricle, and this RV coil electrode connects through internal conductors in the lead and is connected both to terminals 12 and 13. The lead system 20 also includes an SVC electrode 23, positioned a distance back from the distal end of the electrode as indicated. The SVC electrode is connected to terminal 14.

The defibrillator/pacemaker 10 is a programmable microprocessor-based system, with a microprocessor indicated by reference number 30. Microprocessor 30 operates in conjunction with a memory 32, which contains parameters for various pacing and sensing modes. Microprocessor 30 includes means for communicating with an internal controller, in the form of an RF receiver/transmitter 34. This includes a wire loop antenna 35, whereby it may receive and transmit signals to and from an external controller 36. In this manner, programming inputs can be applied to the microprocessor of the defibrillator/pacemaker after implant, and stored data on the operation of the system in response to patient needs can be read out for medical and analysis.

In the defibrillator/pacemaker of FIG. 1, the tip and RV coil, connected through leads 11 and 12, are applied to a sense amplifier 15, whose output is shown connected to an R wave detector 16. These components serve to amplify and sense the QRS wave of the heart, and apply signals indicative thereof to a microprocessor 30. Among other things, microprocessor 30 responds to the R wave detector 16, and provides pacing signals to a pace output circuit 17, as needed according to the programmed pacing mode. Output circuit 17 provides output pacing signals to terminals 11 and 12, which connect as previously indicated to the tip and RV coil electrodes, for normal pacing.

The DF portion of the defibrillator/pacemaker FIG. 1 includes a high energy output pulse generator 40, which operates under the control of microprocessor 30, as indicated. Pulse generator 40 is connected to terminals 13 and 14, which connect to the RV coil and SVC as previously mentioned. In this manner, DF shocks can be provided through the endocardial lead system 20 for defibrillation when called for by the microprocessor, and specifically the software implementation of control algorithms.

Figure 2:
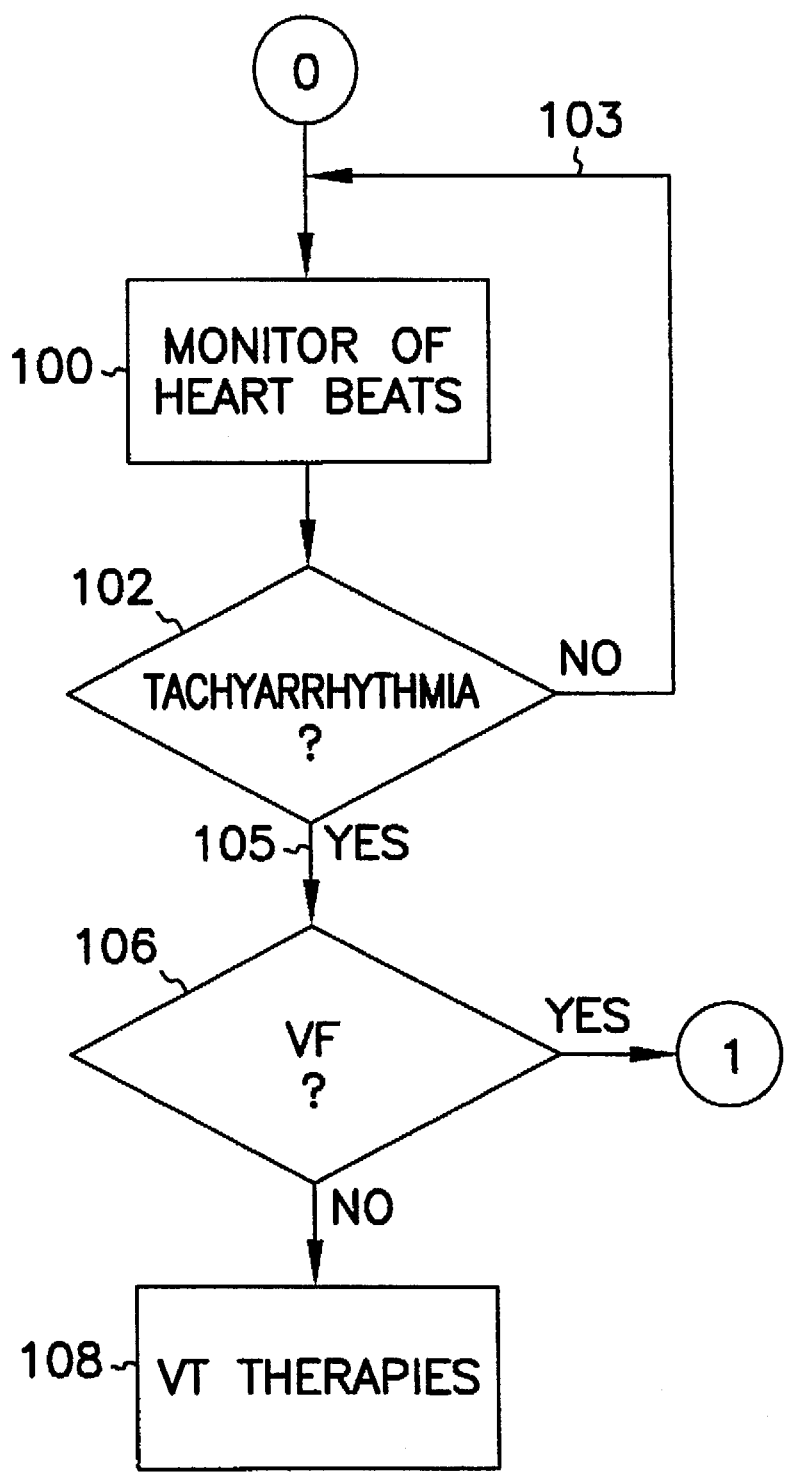
FIG. 2 is a flow chart illustrating a mode of operation of the defibrillator/pacemaker of FIG. 1 in detecting tochyarrhythmia and VF.

FIG. 2 illustrates overall modes of operation of the system. In paced operation, the system operates under programmed control to monitor heart beats occurring in the patient's heart. This is indicated by block 100 in FIG. 2. As is generally known in the art, such monitoring is accomplished through the sense amp and R wave detector, elements 15 and 16 in FIG. 1, and microprocessor control. Pacing may be administered as needed, depending upon the type of pacing functions provided in the defibrillator/pacemaker.

Decision block 102 tests whether a tochyarrhythmia has been detected. This is done through analysis of electrical signals from the heart under control of the microprocessor and its stored program. If such condition is not detected, control branches via path 103 back to the heart beat monitor block 100, and the process continually repeats.

If, however, a tachycardia arrhythmia condition is detected at decision block 102, control passes via path 105 to decision block 106, which tests for VF, through analysis of heart signals as is known in the art. If VF is not detected, control branches to block 108 for VT therapies, as is known in the art.

If at block 106, VF is detected, control branches to the VF therapies of FIGS. 4 and 5, which include coordinated DF shocks according to the present invention, as described in greater detail below.

Figure 3:
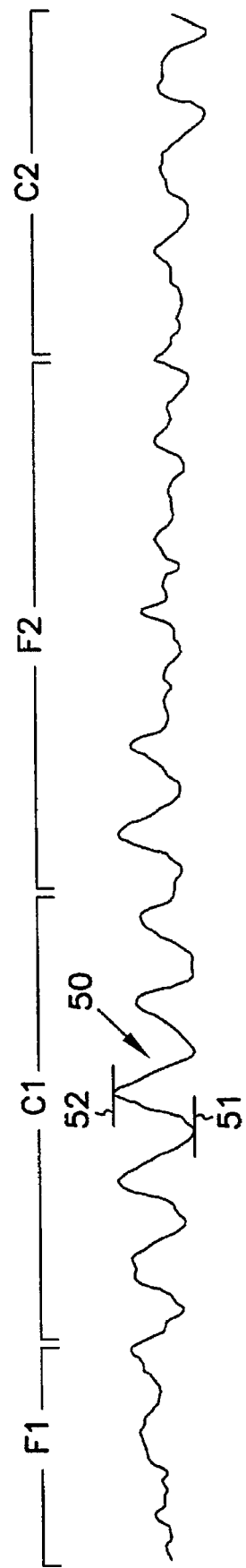
FIG. 3 is a waveform of a morphology signal from a heart in VF.

FIG. 3 illustrates a morphology signal such as would be detected by sensing amp 18, from the signal appearing across the RV coil-SVC in an endocardial lead. For other types of lead systems, similar or corresponding signals would be present. In FIG. 3, the wave form is the voltage signal at the sense amp 18. The vertical axis represents amplitude, and the horizontal axis represents time. As used herein, the heart (morphology) signals are represented as what is considered as normal polarity of signals from the heart. Thus, references to increasing signal, positive slope, or upslope, are all with reference to normal polarity. Reversing the polarity of the leads would cause reversal of the polarity of the signal, in which case a corresponding reversal of positive slope to negative slope. If the polarity of sensing is changed, the system could coordinate DF shocks on negative-going signals, but the data to date suggests this might not be as effective. Alternatively, the absolute value of the sensed signal could be used, which would correspond to either positive or negative polarity signals. For purposes of the preferred embodiment, positive or normal polarity will be assumed.

In FIG. 3 Zones F1 and F2 show regions of fine VF. Zones C1 and C2 show coarse VF complexes. Within complex C1, a single peak feature of the complex is indicated by reference number 50. The difference in amplitude between the amplitude extremes, 52, 51, indicates the peak-to-peak amplitude calculation which is used as a part of the method of the invention.

Figure 4:
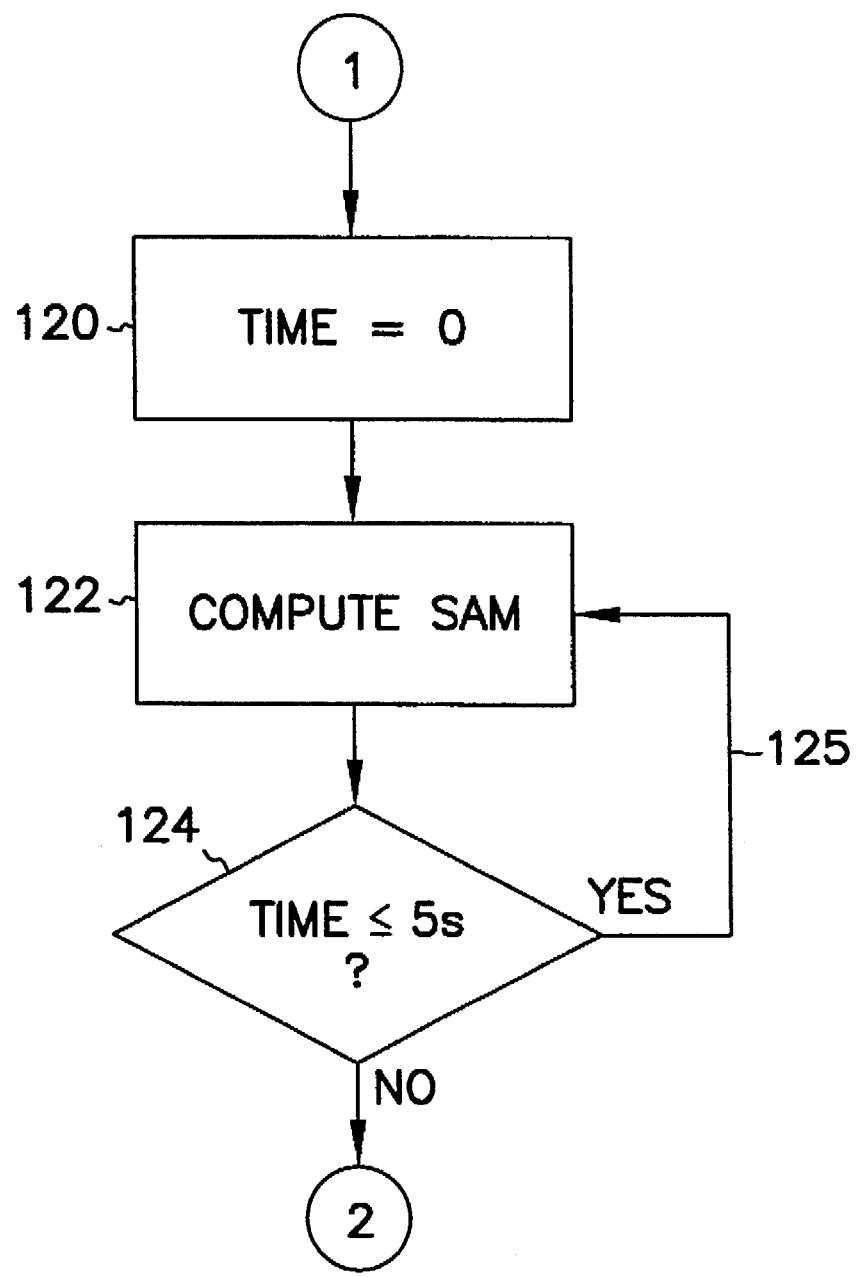
FIG. 4 is a flow chart illustrating the computation of Standard Amplitude of Morphology (SAM) by the system.

In FIG. 4, the symbol "1" in the circle is the link from FIG. 2. Upon occurrence or detection of a VF condition, the Standard Amplitude of Morphology (SAM) is computed for a five-second interval. The five seconds is programmable, and a different value may be used. At block 120, which is reached after a VF has been detected in FIG. 2, a time is initialized at a starting or zero point. Flow in branches to step 122, where the SAM is computed, based upon peak-to-peak value readings, as indicated in FIG. 3. Preferably, this is accomplished by continually taking samples of the morphology signals and comparing them with previously obtained samples. When such comparison shows a trend reversing, i.e., from decreasing to increasing, or from increasing to decreasing in value, a bottom or top, i.e., a peak, negative or positive, has been reached. Such peak values are then stored for comparison with other peak values as part of the SAM calculation. For each peak occurring in a complex, the high and low values, and hence the peak-to-peak values, are calculated and stored.

Flow then proceeds to decision block 124, where the time for this five-second interval is tested. If the five seconds (or other programmable interval) has not passed, flow branches back via path 125 to the computation block 122, and computation detection of peaks and computation of peak-to-peak value continues. If, however, the time has exceeded or equaled the five-second set interval, control passes to block 126. At this point, the SAM is calculated, as being the average of the five largest peak-to-peak measurements during the five-second interval in FIG. 4. This is done through recall, comparison, and calculation based upon the stored peak values.

Figure 5:
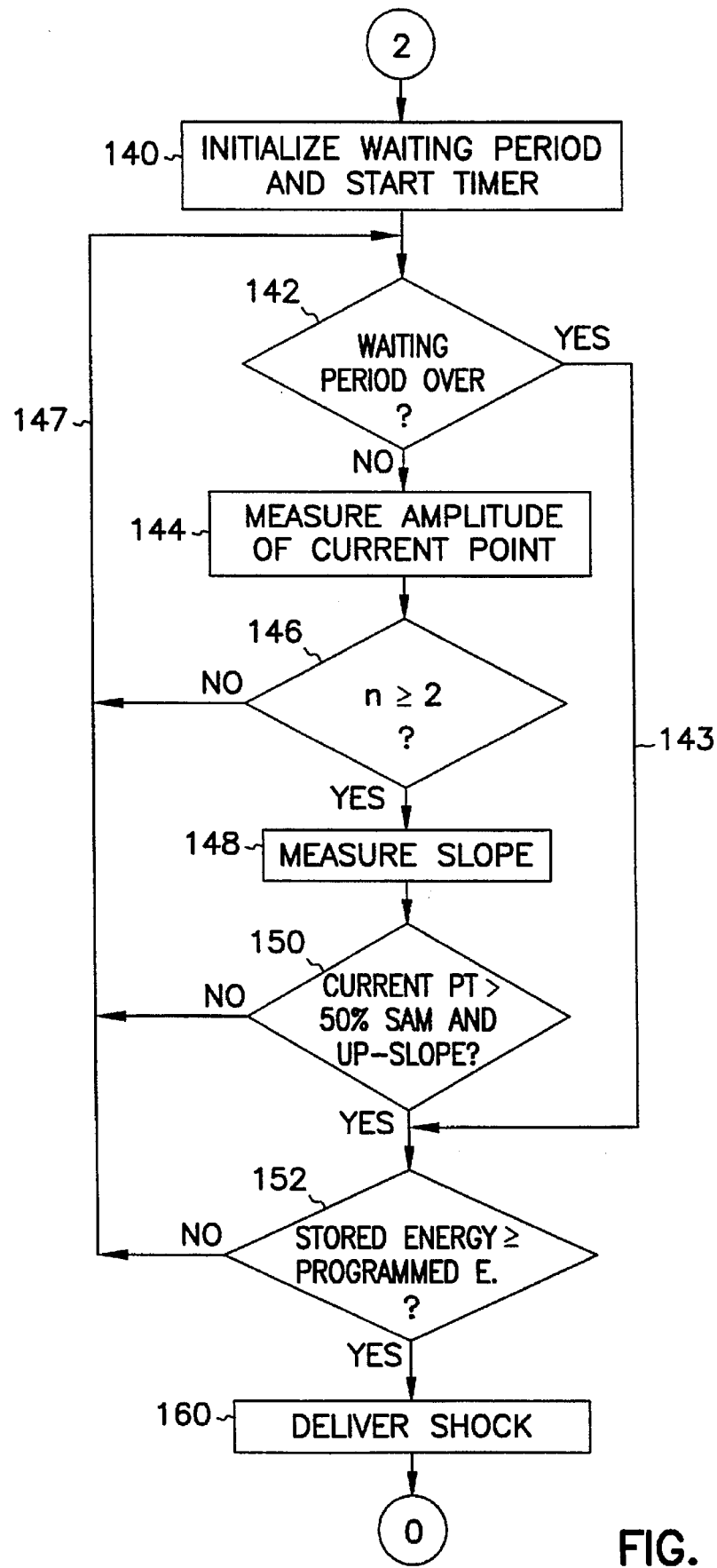
FIG. 5 is a flow chart illustrating the operation of the invention for delivering DF shocks coordinated with a VF feature.

FIG. 5 shows the operation of the system for delivering coordinated DF shocks based on sensed VF complex features. The start of FIG. 5 is reached from the flow chart of FIG. 4. At step 140 n (the count for CMC discussed below) is set to zero, the waiting period is initialized, and the waiting period timer is started. This defines the time period during which coordinated DF shocks may be attempted, and after which the system will switch to asynchronous DF shocks. This time period is preferably programmable as one of the programming parameters for the defibrillaor/pacemaker 10 microprocessor. This time period must be kept within reasonable physiological limits, before going to asynchronous mode. For example, a period of 10 seconds may be appropriate. Decision block 142, which potentially is looped through multiple times, tests whether the waiting time limit programmed for coordinated DF shocks has passed. If not, control passes to step 144, where the amplitude of the morphology signal for the present or current point is taken by sense amp 18. This could be done by hardware or software in analyzer 19, part of which could also be done by software in microprocessor 30.

The amplitude of the current point is compared to the previously computed value of SAM, at step 144. If it has a peak-to-peak amplitude greater than or equal to 50% of SAM, it is identified as a Candidate Morphology Complex (CMC), and a count of CMC is incremented by one. The CMC count n is tested at step 146. If the count is equal to or above the programmed number (which is 2, in FIG. 5, but which could be changed by programming the system), control passes to step 148. If not, control returns to path 147 and the start of the sequence.

At step 148 the system tests whether the current point is on an upslope, i.e. has a positive slope. This is done by comparing the amplitude of the current point to the amplitude of the previous point, to determine the trend.

Step 150 then tests whether the current point is at greater than 50% of the SAM value, and has a positive slope. If either of these is not met, then control branches to path 147, to repeat the loop. If both of these conditions are met, then control passes to step 152. Also, if the waiting period had timed out in step 142, without finding the required conditions for coordinated DF shocking, then control would have passed via path 143 to step 152, also.

At step 152, the system tests whether the stored energy in the high energy output 40 has reached the pre-programmed level. It may take several seconds to do so, depending on the set level and the battery condition. If the energy level has not been reached, control passes via 147 to loop again. After the energy level has been reached at step 152, control passes to step 160, which causes the DF pulse generator 40 to deliver the DF shock.

Figure 6:
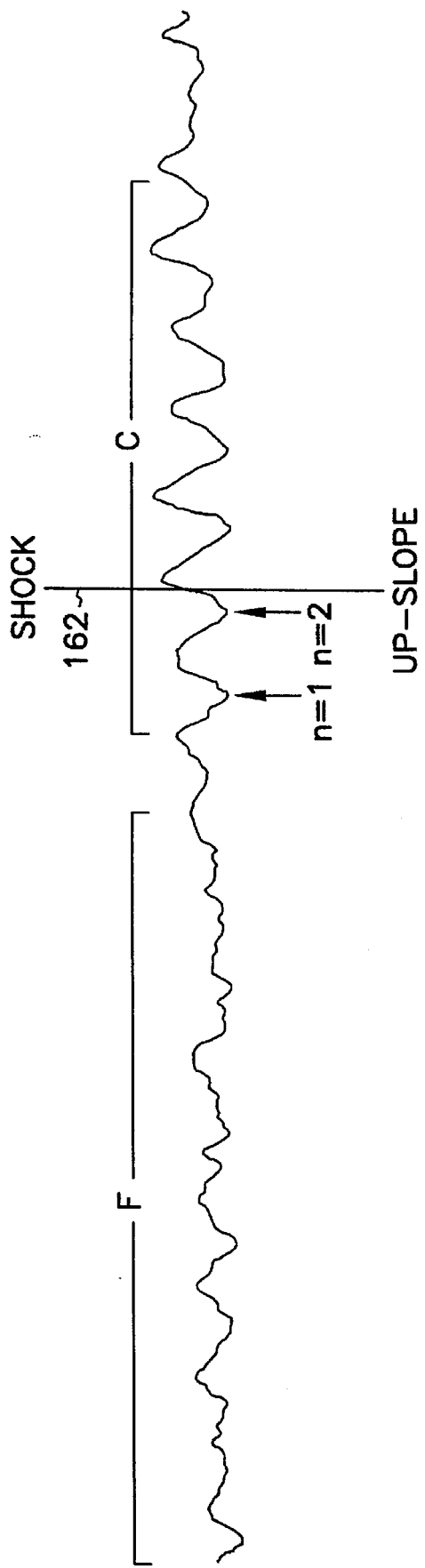
FIG. 6 is a waveform of a morphology signal from a heart showing fine VF and coarse VF complexes, and illustrating the delivery of the DF shock coordinated with a VF feature.

This is illustrated in the waveform of FIG. 6, which is a morphology signal similar to FIG. 3. The zone labelled F is a area of fine VF, and the zone C is a coarse VF complex. As the VF is occurring in real time, the system is sensing and monitoring the morphology signal. After the first major peak indicated the system has determined that a peak of a possible coarse VF complex has occurred, and the count is incremented at the peak "n=2". Assume, as is the case in FIG. 6, that it is in fact the start of a VF complex. The second peak "n=2"is counted as 2. On the next upslope, as the amplitude passes 50% of the Standard Amplitude of Morphology (SAM), on a CMC peak count of 2 or more, and with a positive slope, and if there is sufficient energy at step 152, the decision is made based on these criteria to deliver the DF shock. The microprocessor 30 and pulse generator 40 then deliver the shock shortly thereafter based on this decision. The DF shock is indicated at line 162.

Following the delivery of the DF shock, the sensing circuits of the defibrillator/pacemaker check to see whether the shock was successful, that is, whether the VF has stopped. This is represented by a return to point "0"at the start of FIG. 2. If not successful, and if VF continues, this is detected in FIG. 2, and control passes again to FIG. 5 to repeat the VF therapy. The waiting period (steps 140, 142) for the second or higher passes can preferably be by-passed (or at least separately programmed from the first pass). Then if the first shock fails, the process of sensing and coordination for delivery for a second shock can begin immediately.

We claim:

1. A method of treating ventricular fibrillation, comprising the steps of:
    a) monitoring a signal representative of ventricular electrical activity during a period of ventricular fibrillation;
    b) detecting in the monitored signal, the occurrence of coarse VF complexes;
    c) analyzing coarse VF to determine upslope; and
    d) delivering a DF shock during the upslope portion of a complex.

2. A method according to claim 1, including the step of counting occurrences of coarse VF complexes, and coordinating the delivery of the DF shock with the upslope of a predetermined numbered occurrence of coarse VF complex.

3. The method of claim 1 wherein the step of monitoring comprises monitoring the morphology signal, across proximal and distal shocking coils of an endocardial lead, and wherein the step of delivering a DF shock includes applying a pulse of electrical energy to the endocardial lead.

4. The method of claim 1 wherein the steps of detecting and analyzing the occurrence of a coarse VF complex includes sensing when the amplitude of the VF signal is greater than a predetermined value with a positive slope or rate of change.

5. The method of claim 1 wherein the step of delivering a DF shock includes timing the shock based on when the amplitude of the VF signal is greater than a predetermined value and has a positive slope or rate of change.

6. A method of treating ventricular fibrillation, comprising the steps of:
   a) monitoring a signal representative of ventricular electrical activity during a period of ventricular fibrillation;
   b) detecting and counting the occurrence of coarse VF complexes; and
   c) delivering a DF shock during the nth counted complex, where n is a number greater than or equal to 2 and less than or equal to about 9.

7. The method of claim 6 wherein the step of monitoring comprises monitoring the morphology signal, between proximal and distal shocking coils, of an endocardial lead, and wherein the step of delivering a DF shock includes applying a pulse of electrical energy to the endocardial lead.

8. The method of claim 6 wherein the step of detecting the occurrence of a coarse VF complex includes sensing when the amplitude of the VF signal is greater than a predetermined value with a positive slope or rate of change.

9. The method of claim 6 wherein the step of delivering a DF shock on the nth complex includes timing the shock based on when the amplitude of the VF signal is greater than a predetermined value and has a positive slope or rate of change.

10. A method of treating ventricular fibrillation, comprising the steps of:
    a) monitoring a signal representative of ventricular electrical activity during a period of ventricular fibrillation;
    b) detecting the occurrence of coarse VF complexes;
    c) analyzing coarse VF complexes to determine upslope; and
    d) delivering a DF shock during the upslope of the nth counted complex, where n is a number greater than or equal to 2 and less than or equal to about 9.

11. A method according to claim 10 wherein the step of analyzing includes counting coarse VF complexes.

12. The method of claim 10 wherein the step of monitoring comprises monitoring the morphology signal, between proximal and distal shocking coils, of an endocardial lead, and wherein the step of delivering a DF shock includes applying a pulse of electrical energy to the endocardial lead.

13. The method of claim 10 wherein the steps of detecting and analyzing the occurrence of a coarse VF complex includes sensing when the amplitude of the VF signal is greater than a predetermined value with a positive slope or rate of change.

14. The method of claim 10 wherein the step of delivering a DF shock on the nth complex includes timing the shock based on when the amplitude of the VF signal is greater than a predetermined value and has a positive slope or rate of change.

15. A method of determining when to deliver a DF shock to a heart in ventricular fibrillation, comprising the steps of:
    a) monitoring a signal representative of ventricular electrical activity during a period of ventricular fibrillation;
    b) detecting the occurrence of coarse VF complexes as intervals of increase of the absolute value of the monitored signal; and
    c) selecting the time for DF shock delivery based on when the absolute value of the monitored VF signal reaches a predetermined value during a period of increasing rate.

16. A method of determining when to deliver a DF shock to a heart in ventricular fibrillation, comprising the steps of:
    a) monitoring a signal representative of ventricular electrical activity during a period of ventricular fibrillation;
    b) measuring the amplitude of the monitored signal;
    c) determining the rate of change of the amplitude of the monitored signal; and
    d) selecting the time for DF shock delivery based on the amplitude of the monitored signal, a predetermined value during fibrillation, and whether the rate of change of the amplitude is positive.

17. A method of claim 16 wherein the step of measuring includes repeated sampling of the monitored signal, and the step of determining rate of change includes comparing samples of the monitored signal over a small increment of time.

18. A method of treating ventricular fibrillation, comprising the steps of:
    a) monitoring a heart signal representative of ventricular electrical activity;
    b) detecting the presence of ventricular fibrillation
    c) during VF, detecting the occurrence of coarse VF complexes by measuring the monitored signal; and
    d) for the nth coarse VF complex, where n is greater than or equal to 2 and less than or equal to 9, delivering a coordinated DF shock based on the a predetermined value for the amplitude of the monitored signal, and whether the amplitude has a positive the rate of change.

19. A method according to claim 10 further including the step of delivering at least one asynchronous DF shock if the VF is not terminated by the delivery of coordinated DF shocks.

20. A defibrillator, comprising:
    a lead system for placement in electrical contact with the ventricle of the heart;
    a sensing system, attached to the lead system for monitoring ventricular electrical activity, which detects the presence of VF, and during VF to detect coarse VF complexes;
    a DF control system for controlling delivery of DF shocks through the lead system to the ventricle, the control system responsive to the sensing system to deliver a DF shock when the sensed VF complex increases to a predetermined value with a positive rate of change.

21. The defibrillator according to claim 20 wherein the DF control system comprises a counting subsystem which counts the occurrence of VF complexes, and the DF control system delivers a DF shock coordinated with the nth coarse complex, where n is greater than or equal to 2 and less than or equal to about 9.

22. The defibrillator according to claim 21 wherein the DF control system delivers the coordinated shocks during an interval following onset of VF, and at least one asynchronous DF shock if the VF is not terminated by the coordinated shocks.

* * * * *